United States Patent [19]

Berlin et al.

[11] Patent Number: 5,854,267
[45] Date of Patent: Dec. 29, 1998

[54] METHOD FOR PREVENTING HEARTBURN

[75] Inventors: Roger Berlin, Haverford, Pa.; Thomas N. Gates, Bonita Springs, Fla.; Thomas Simon, Berwyn, Pa.

[73] Assignees: Merck & Co., Inc., Rahway; Mc Neil-PPC, Inc., Skillman, both of N.J.

[21] Appl. No.: 459,182

[22] Filed: Jun. 2, 1995

(Under 37 CFR 1.47)

[51] Int. Cl.$^6$ .................................................. A61K 31/425
[52] U.S. Cl. .............................................. 514/370
[58] Field of Search .............................................. 514/370

[56] References Cited

U.S. PATENT DOCUMENTS 4,283,408   8/1981   Hirata et al. ............................ 424/270

FOREIGN PATENT DOCUMENTS 0 492 247 A1   9/1991   European Pat. Off. .

OTHER PUBLICATIONS

Pepcid AC acid Control–Product Monograph, pp. 1–32 (1994).
Yamada, "Textbook of Gastroenterology", vol. 1, pp. 1214, 1215, and 1232 (1995).
Chremos, A.N., "Clinical Pharmacology of Famotidine: A Summary", J. Clin. Gastroenterol, vol. 9 (Suppl. 2), pp. 7–12 (1987).
Thompson et al., "Heartburn and globus in apparently healthy people", CMA Journal, vol. 126, pp. 46–48 (1982).
Laskin et al., "Pharmacodynamics and Dose–Response Relationship of Famotidine: A Double–Blind Randomized Placebo–Controlled Trial", J. Clin. Pharmacol, vol. 33, pp. 636–639 (1993).
McCallum et al., "MK–208, A Novel Histamine H2–Receptor Inhibitor with Prolonged Antisecretory Effect", Digestive Diseases and Sciences, vol. 30, pp. 1139–1144 (1985).
Gitlin et al., "A Multiclinic Double–Blind Dose Ranging Study Evaluating the Efficacy and Safety of Famotidine in the Healing of Active Duodenal Ulcer as compared to Placebo", Amer. Journal of Gastroenterology, vol. 80, p. 840 (1985).
Miyoshi et al., "Clinical Evaluation of Famotidine on Acute Gastric Mucosal Lesions Associated with Acute Gastritis and Chronic Gastritis–Dose Finding Study by the Double Blind Comparative Method–", Naika Hokan, vol. 34, pp. 442–457.
Douds, Andrew C. and J. Douglas Maxwell, "Over the Counter H2 receptor Antagonists", BMJ, (Letters), vol. 309, p. 1156 (1994).
Cooper, J.R.B., "Increase the risks to offshore workers", BMJ, (Letters), vol. 309, pp. 1156–1157 (1994).
Simon et al., "Self–Directed Treatment of Intermittent Heartburn: A Randomized, Multicenter, Double–Blind(DB), Placebo(P)–Controlled Evaluation of Famotidine(FAM) 5, 10 & 20MG and Antacid(AA)", Esophageal, Gastric, and Duodenal Disorders, p. A181 (1994).
MSD Merck Sharp & Dohme, "Pepcid Insert" 1986.
Stedman's Medical Dictionary (1995) p. 356, Pub. Houghton Mifflin Company.
Koss et al., Gastroenterology, 98(6) A71 (1990).
Simon et al., Gastroenterology 106(4 Suppl.) 1994.

*Primary Examiner*—Phyllis G. Spivack
*Attorney, Agent, or Firm*—Richard S. Parr; Melvin Winokur

[57] ABSTRACT

A method for preventing heartburn episodes in a patient susceptible to suffering heartburn episodes following ingestion of heartburn-inducing food or beverage, comprising administering to the patient, 30 minutes prior to consumption by the patient of the food or beverage, a composition comprising an amount of famotidine of 10 mg.

1 Claim, 3 Drawing Sheets

METHOD FOR PREVENTING HEARTBURN

BACKGROUND OF THE INVENTION

Heartburn, or pyrosis, is a sensation of pain or burning located substernally or high in the epigastrium with radiation into the neck and occasionally to the arms, associated with regurgitation of acid-peptic gastric juice into the esophagus. Occasional heartburn is common in normal persons, but frequent and severe heartburn is generally a manifestation of esophageal dysfunction. Heartburn may result from abnormal motor activity or distention of the esophagus reflux of acid or bile into the esophagus, or direct esophageal mucosa irritation (esophagitis).

Heartburn is most often associated with gastroesophageal reflux. In this setting, heartburn typically occurs after a meal, with stooping or bending, or when the patient is supine. It may be accompanied by the spontaneous appearance in the mouth of fluid which may be salty, sour, or bitter and green or yellow. Heartburn may arise following the ingestion of certain foods (e.g. citrus fruit juices) or drugs (e.g. alcohol or aspirin).

Reflux esophagitis consists of esophageal mucosal damage resulting from reflux of gastric or intestinal contents into the esophagus. Esophagitis, an inflammation of the esophagus from regurgitation of acid gastric contents, producing substernal pain, develops when the mucosal defenses that normally counteract the effect of injurious agents on the esophageal mucosa succumb to the onslaught of the refluxed acid pepsin or bile. Mild esophagitis shows microscopic changes of mucosal infiltration with granulocytes or eosinophils, hyperplasia of basal cells, and elongation of dermal pegs. Erosive esophagitis shows endoscopically visible damage to the mucosa in the form of marked redness, friability, bleeding, superficial linear ulcers, and exudates.

Famotidine (available from Merck & Co., Inc., Whitehouse Station, N.J., under the name PEPCID®), an antagonist of the histamine $H_2$ receptor, is 3-{{{2-[(aminoiminomethyl)amino]-4-thiazolyl]methyl]thio]-N-(aminosulfonyl)propanimidamide, having the structural formula:

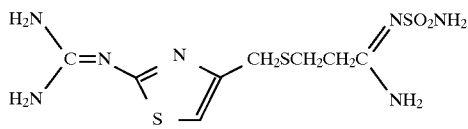

The primary clinically important pharmacologic activity of famotidine is inhibition of gastric secretion. Both acid concentration and volume of gastric secretion are reduced by famotidine. Famotidine is used to treat acid-related disorders such as gastric and duodenal ulcer, gastroesophageal reflux disease and Zollinger Ellison syndrome. Its safety and efficacy have been well established in controlled clinical studies. It is used by over 31 million patients worldwide.

Trials have shown famotidine to be beneficial in a dose dependent manner in relief of symptoms associated with ulcerations and gastritis.

Gitlin et al., *Amer. Journal of Gastroenterololg* (1985) vol. 80 pp. 840 examines famotidine efficacy in the treatment of active duodenal ulcers. The results suggest that duodenal ulcer healing rates are famotidine dosage dependent. 20 mg twice daily, 40 mg twice daily and 40 mg at bedtime were administered over a four week period. Healing rates of 67, 75, 70%, respectively, were seen.

Similarly, Miyoshi et al., *Naika Hokan* (1987) vol. 34 pp. 442–457 demonstrates that the efficacy of famotidine as a gastritis therapy is dose-related. Miyoshi et al. evaluated dosage regimens of 5, 10, or 20 mg twice daily in the treatment of gastritis symptom relief. Patients treated with 10 to 20 mg of famotidine had fewer erosions and mucosal haemorrhages than those treated with 5 mg famotidine.

McCallum et al., *Dig. Dis. Sci.* (1985) vol. 30 pp. 1139–1144 describes a study of healthy patients demonstrating that 5 mg of famotidine produces has an effect on gastric acid secretion. Laskin et al., *J. Clin. Pharmacol.* (1993) vol. 33 pp. 636–639 describes a study demonstrating that single doses of 5 and 10 mg of famotidine produces statistically significant decreases in intragastric acidity, beginning at 90–100 minutes and persisting for approximately 9 hours.

Applicants have now found that administration of famotidine, prior to consumption by patients of heartburn-inducing food or beverage, to patients who ordinarily experience heartburn episodes following consumption of such meals, is an effective means for preventing or minimizing symptoms associated with heartburn. Applicants have found that heartburn episodes can be prevented in patients ordinarily susceptible to heartburn episodes, if famotidine is administered in doses of between 5 mg and 20 mg, prior to ingestion of heartburn-inducing food and beverage. Applicants have also found that the risk of experiencing heartburn episodes can be reduced in patients ordinarily susceptible to heartburn episodes if such doses of famotidine are administered prior to ingestion of heartburn-inducing food and beverage. Applicants have also found that heartburn episodes in patients ordinarily susceptible to heartburn episodes can be relieved if such doses of famotidine are administered prior to ingestion of heartburn- inducing food and beverage.

Applicants have also found that the effectiveness of such treatment is not dose dependent.

SUMMARY OF THE INVENTION

The invention is a method for preventing heartburn episodes in a patient susceptible to suffering heartburn episodes following ingestion of heartburn-inducing food or beverage, comprising administering to the patient, prior to consumption by the patient of the food or beverage, a composition comprising an amount of famotidine between about 5 mg and 20 mg.

The invention is also a method for reducing the risk of heartburn episodes in a patient susceptible to suffering heartburn episodes following ingestion of heartburn-inducing food or beverage, comprising administering to the patient, prior to consumption by the patient of the food or beverage, a composition comprising an amount of famotidine between about 5 mg and 20 mg.

The invention is also a method for relieving heartburn episodes in a patient susceptible to suffering heartburn episodes following ingestion of heartburn-inducing food or beverage, comprising administering to the patient, prior to consumption by the patient of the food or beverage, a composition comprising an amount of famotidine between about 5 mg and 20 mg.

DETAILED DESCRIPTION OF THE DRAWINGS

FIG. 1 is a graph representing heartburn severity in patients in response to administration to patients of famotidine 5 mg, famotidine 10 mg, famotidine 20 mg, or placebo, and subsequent ingestion by the patients of heartburn-inducing food or beverage.

DETAILED DESCRIPTION OF THE INVENTION

Figure 1:
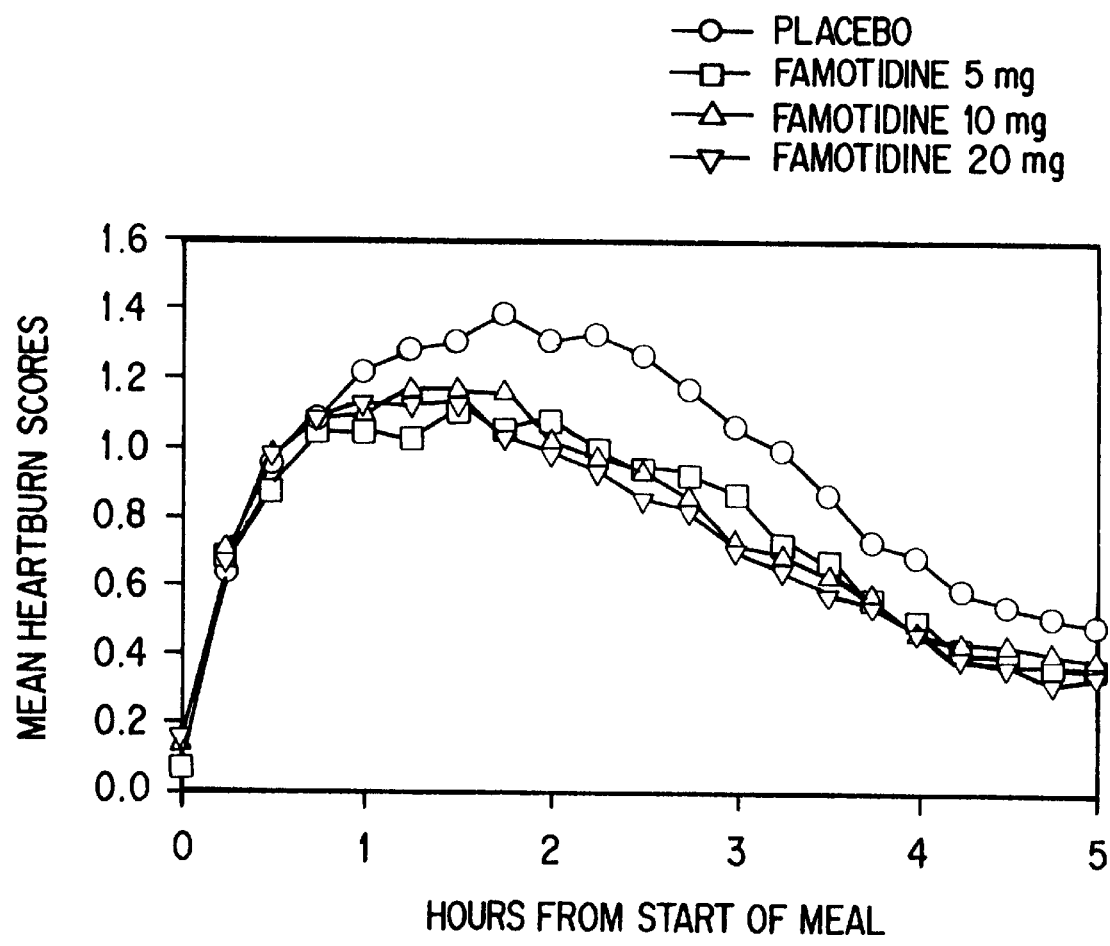

Compositions for use in the present invention contain famotodine in an amount of between about 5 mg and 20 mg. In one embodiment of the invention, the compositions include 5 mg famotidine. In another embodiment of the invention, the compositions include 10 mg famotidine. In another embodiment of the invention, the compositions include 20 mg famotidine.

The compositions may also contain pharmaceutically acceptable carriers. Compositions may be formulated for oral administration in solid or liquid form, for example as effervescent or non-effervescent powders or tablets, capsules, suspensions or dispersions. Compositions may thus be formulated by admixture with pharmaceutically acceptable vehicles additionally containing, as desired, pharmaceutically acceptable adjuvants including thickeners, preservatives, and coloring and flavoring agents.

Powder formulations can be prepared by dry blending ingredients under conditions of controlled temperature and humidity using conventional equipment. Tablet formulations can be prepared by combining the active components with tableting aids, fillers and palatability aids in a conventional manner and tableting on a conventional machine.

In the example shown below, famotidine tablets including 5 mg famotidine and amounts of inactive ingredients hydroxypropyl cellulose, hydroxypropyl methylcellulose, iron oxides, magnesium stearate, microcrystalline cellulose, starch, talc, and titanium dioxide sufficient to prepare an pharmaceutically acceptable tablet for delivery of the active famotidine were prepared, as were tablets including 10 mg famotidine and 20 mg famotidine and appropriate amounts of such inactive ingredients.

The term "preventing heartburn episodes" means precluding symptoms, or reducing the severity of symptoms, associated with heartburn in patients susceptible to heartburn following ingestion of heartburn-inducing food or beverage.

The term "precluding symptoms" means making the experience of symptoms impossible or largely ineffectual by removing the conditions needed for them.

The term "reducing the severity of symptoms" means substantially lowering the degree of pain associated with heartburn symptoms that would ordinarily occur in patients susceptible to heartburn following ingestion of heartburn-inducing food or beverage.

The term "reducing the risk of heartburn episodes" means substantially lowering the tendency of patients susceptible to heartburn, following ingestion of heartburn-inducing food or beverage, to experience symptoms associated with heartburn following ingestion of heartburn-inducing food or beverage.

The term "relieving heartburn episodes" means eliminating or substantially eliminating symptoms, associated with heartburn following ingestion of heartburn-inducing food or beverage.

The term "heartburn-inducing food or beverage" includes foods and beverages commonly associated with heartburn in patients susceptible to food- or beverage-induced heartburn episodes, e.g. tomatoes, chili, coffee, red wine, citrus juice, etc. For purposes of describing the invention, the term "meal" is hereinafter to be understood to mean heartburn-inducing food and/or beverage.

The degree of heartburn pain associated with ingestion of such foods varies among individuals and with food types. Thus, some individuals may be more sensitive to certain heartburn-inducing foods than are other individuals. The tendency for a given individual to experience heartburn in response to ingestion of a particular food or beverage is predictable, however, and the individual is able to determine, prior to ingestion, which food or beverage will induce heartburn symptoms.

A "patient susceptible to suffering heartburn episodes following ingestion of heartburn-inducing food or beverage" means any patient who ordinarily experiences symptoms of heartburn caused by ingestion of heartburn-inducing food or beverage The famotidine compositions are administered prior to consumption by the patient of the heartburn-inducing food or beverage, at a time such that the anti-secretory activity of famotidine will be engaged prior to stimulation, by heartburn-inducing food or beverage, of the acid-secreting parieta cells. Such administration can be within six hours prior to ingestion of the heartburn-inducing food or beverage. In one embodiment, administration is between 30 minutes and 2 hours prior to meal consumption, e.g. I hour prior to meal consumption.

EXAMPLE

Adult male and female subjects having a history of heartburn, acid indigestion, or sour/upset stomach of at least 2 months' duration, with a minimum of three episodes per week, were studied. Subjects had to be able to identify specific foods or beverages that produced their symptoms and had to have used antacids in the past to relieve their discomfort. If not post-menopausal, female subjects had to be practicing an approved form of contraception. A history of serious gastrointestinal conditions, such as duodenal or gastric ulcer, atrophic gastritis within the previous 6 months, esophageal strictures, irritable colon, inflammatory bowel disease, biliary tract disease, or diverticulosis excluded subjects from the trial. Other exclusion criteria included the presence of a clinically significant laboratory abnormality, pregnancy or lactation (among females), recent use of various prescription drugs, particularly $H_2$ antagonists, omeprazole or sucralfate, and a history of substance abuse.

Following an initial screening assessment, eligible subjects were given a validation meal consisting of commercially available chili and burgundy wine. Only subjects who reported at least moderate symptoms of upper gastrointestinal discomfort within 90 minutes after the start of the meal qualified for treatment with placebo, famotidine 5 mg, famotidine 10 mg, or famotidine 20 mg. Subjects were randomly assigned to one of four treatment sequences.

Subjects were given four test meals (identical in composition to the validation meal), with the interval between meals and trial medications approximately 7 days. Trial medication, in tablet form, was administered I h before each test meal. Rescue medication consisting of an antacid with a neutralizing capacity of 56 mEq/two tablet (Maalox® TC) was available throughout the trial for subjects who insisted on additional relief.

Subjects rated the severity of their heartburn, acid/sour/upset stomach, and overall upper gastrointestinal discomfort prior to the validation and four test meals, and at 15 minute intervals thereafter for 5 hours. Symptom severity was rated on a six-point scale as none (0), slight (1), mild (2), moderate (3), severe (4), or very severe (5). Subjects provided a global evaluation of the study treatment at the end of the 5 hour assessment period or immediately prior to administration of rescue medication. Treatments were rated on a five-point scale as ineffective (0), poor (1), fair (2), good (3), or excellent (4). Efficacy was additionally assessed by examining the use of rescue medication and the time to rescue medication in each treatment group.

The tolerability of the four study treatments was determined by recording all adverse experiences reported by subjects during the trial.

Approximately equal numbers of males (58) and females (63) were studied, ranging in age from 20 to 61 years. Subjects had been experiencing meal-provoked gastrointestinal symptoms for approximately 7 years, having an average of 5.6 episodes per week. Ninety-seven subjects (80%) indicated that the validation meal produced symptoms similar to those provoked by a typical meal, and the severity of symptoms following the validation meal was rated as about the same or worse by 83% of subjects.

Figure 3:
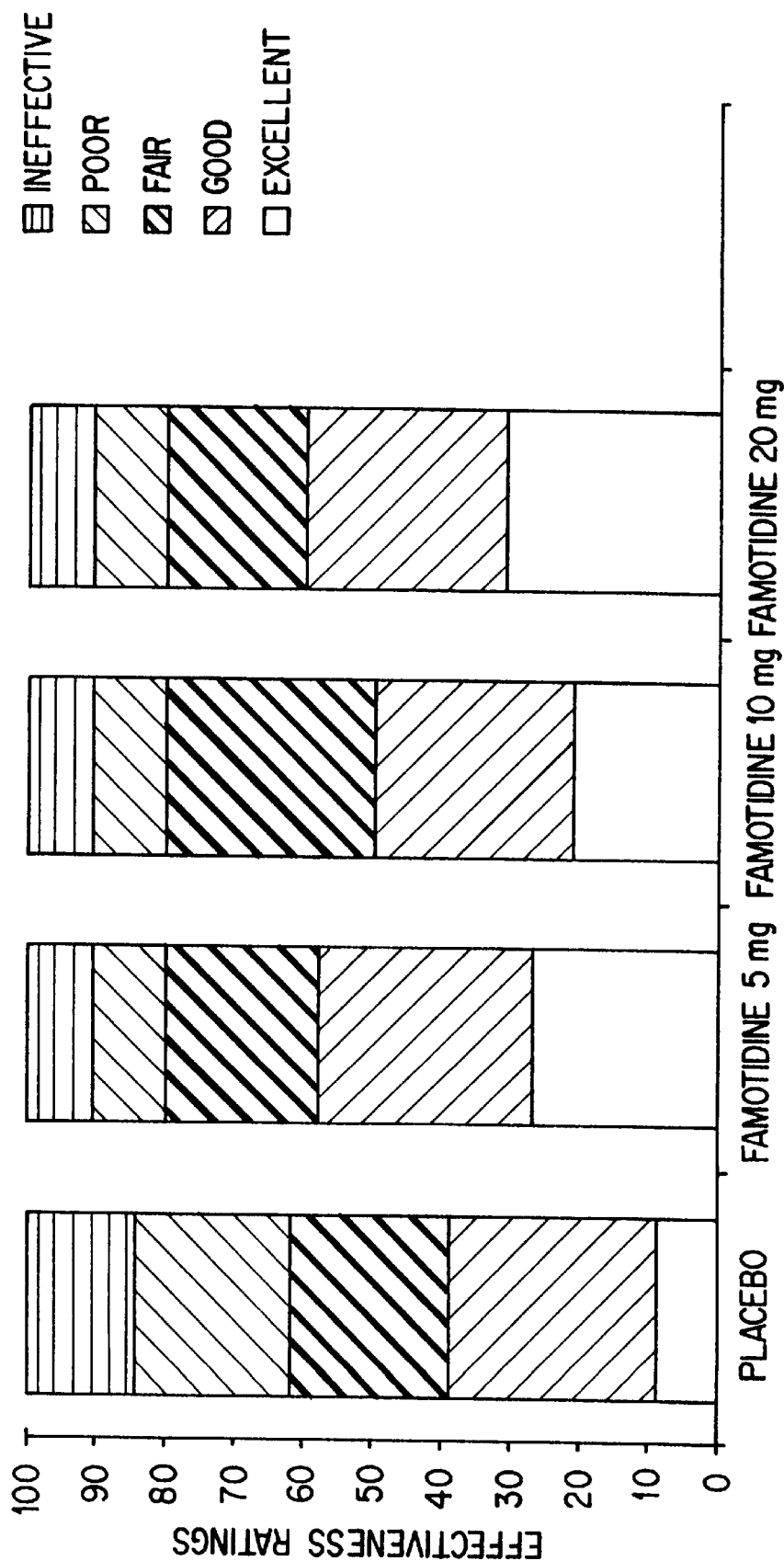
FIG. 3 shows global evaluations of effectiveness based on subject ratings of famotidine administrations as excellent, good, fair, poor or ineffective.

Global evaluations of study medication were significantly more favorable following all three doses of famotidine than following placebo for all four meals combined (p<0.001). More than half of all subjects receiving famotidine (54–63%) rated the drug as either "excellent"or "good" versus only 38% of subjects receiving placebo. The global evaluations of all treatments for the four test meals combined are shown in FIG. 3.

A peak heartburn rating was recorded for each participant. Each individuals' peak heartburn rating was ranked in a manner consistent with the symptom severity evaluation described above. Significantly milder peak heartburn ratings were evident following treatment with all three doses of famotidine compared to placebo (p<0.001 for famotidine 5 mg and famotidine 20 mg versus placebo; (p=0.004 for famotidine 10 mg versus placebo). Approximately three-quarters of famotidine subjects (74–76%) rated their peak heartburn severity as "mild", "slight", or "none". In contract, only 57% of subjects gave similar ratings following placebo treatment.

As shown in FIG. 1, mean heartburn severity tended to be equivalent in the placebo and famotidine dosage groups for the first hour, but for the remainder of time, it was greater in the placebo group than in the famotidine groups. Mean AUC scores (area under the curve) for heartburn across the 5 hour evaluation interval were significantly lower than in the famotidine 5-, 10-, and 20-mg dosage groups than in the placebo group (FIG. 2).

Figure 2:
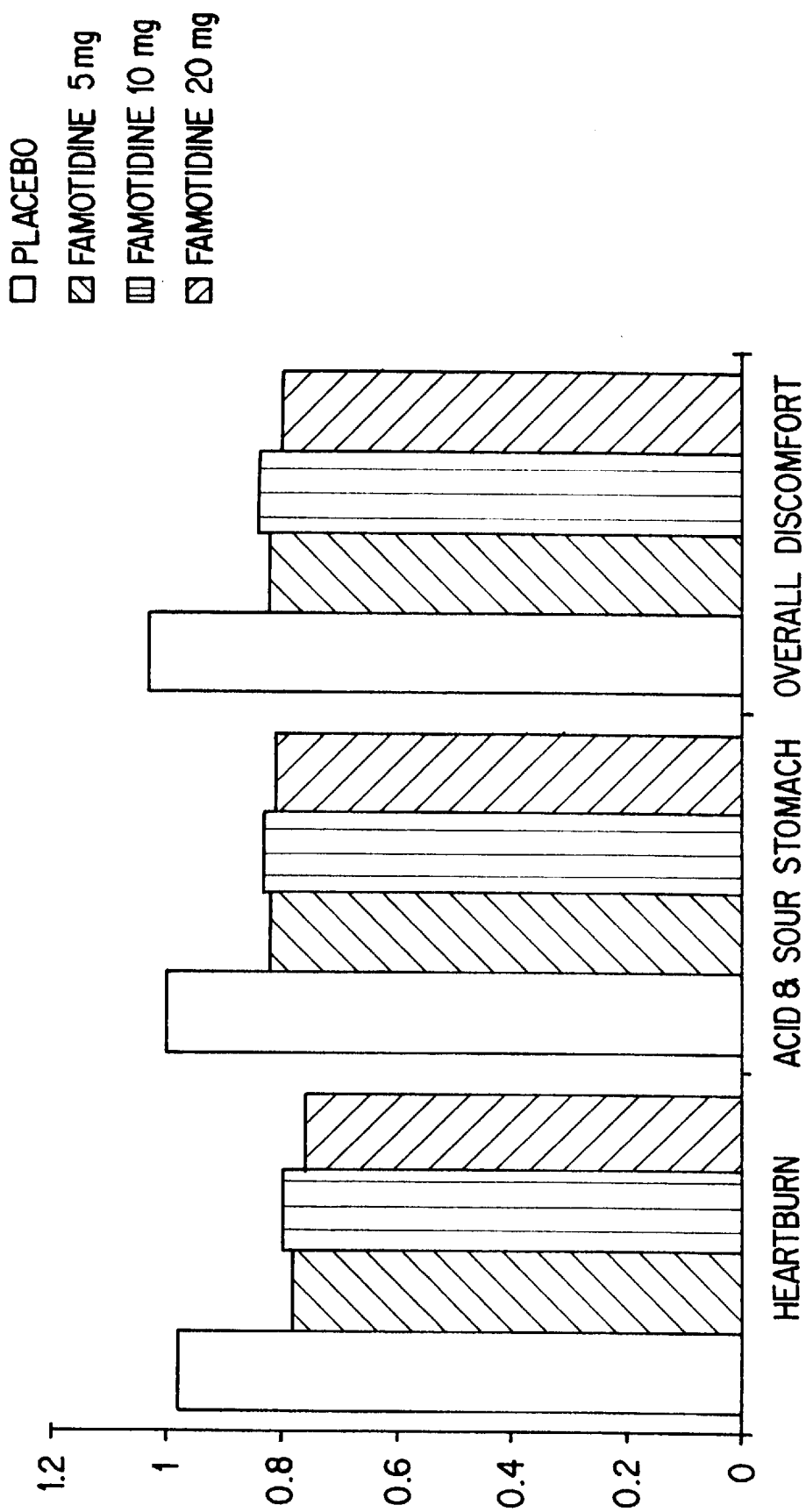
FIG. 2 is a graph showing mean area under the curve scores for heartburn severity, acid sour stomach and overall discomfort.

FIG. 2 also shows that mean AUC scores across the 5 hour assessment period for acid/sour stomach and overall discomfort were significantly smaller for each of the famotidine dosages than for placebo ($p \leq 0.025$ for acid/sour stomach; $p \leq 0.008$ for overall discomfort). In addition, peak rating of both acid/sour stomach and overall discomfort were also milder with famotidine prophylaxis than with placebo. Peak acid/sour stomach was rated as "mild", "slight", or "none" by 73%, 69%, and 68% of subjects following treatment with 5, 10, and 20 mg famotidine, respectively, and by 54% of subjects following placebo treatment. Similar percentages of subjects in the three famotidine dosage groups (77%, 66%, 74%) rated their peak overall discomfort as "mild" or less compared to only 54% of those treated with placebo. The comparison with placebo was statistically significant for all three dosages of famotidine for acid/sour stomach (p<0.034) and was statistically significant for the 5- and 20-mg dosages for overall discomfort (p<0.001).

A rescue antacid was used by only 17–18% of subjects in the three famotidine dosage groups compared to 37% of those treated with placebo (p<0.001). The differences between the famotidine and placebo groups were most evident 90 minutes following test meal ingestion.

With one exception, the differences between the three famotidine dosage groups were not statistically significant for any of the efficacy parameters ($p \geq 0.09$), nor was there evidence of a carryover effect of previous treatment ($p \geq 0.09$). The significant difference between the dosage groups was for overall discomfort where peak ratings following the 5- and 20-mg dosages were milder than those after 10 mg ($p \leq 0.019$).

A total of 61 subjects reported an adverse experience during the trial, with the incidence being approximately equal during each of the four treatment periods. No subject had a serious adverse experience during this trial, nor did any subject discontinue the study prematurely for safety reasons.

The results of the study show that administration of famotidine 1 h before a food and beverage challenge was significantly more effective than placebo in preventing provoked upper gastrointestinal symptoms. Peak ratings of heartburn and acid/sour stomach were significantly milder following administration of single oral doses of famotidine 5, 10, and 20 mg compared to placebo, and approximately three-quarters of subjects rated these symptoms as "none" to "mild" following prophylactic treatment with famotidine compared to slightly more than half following placebo. In addition, overall discomfort was rated as "mild" or less by a larger percentage of subjects following famotidine doses of 5, 10, and 20 mg (77%, 66%, and 74% respectively) than following placebo (54%). This difference was only statistically significant, however, for the 5- and 2-mg dosages. Global evaluations performed at the end of each test period also significantly favored famotidine over placebo, with 54–63% of subjects rating famotidine 5, 10, and 20 mg as "good" or "excellent" compared to only 38% of subjects for placebo. Consistent with these finding, rescue antacids were used by a significantly smaller percentage of subjects following famotidine treatment compared to placebo (17–18% versus 37%).

With the exception of peak overall discomfort ratings, there were no significant differences among the three famotidine dosages in this trial for any of the efficacy parameters evaluated, indicating that a dose as low as 5 mg was as effective as higher doses of 10 and 20mg.

Famotidine was well tolerated in this trial, with the type and frequency of reported adverse experiences similar to those observed with placebo. There was no distinction in the tolerability profile among the three famotidine dosages, confirming the notable absence of any dose-related change in the incidence of side effects reported in other investigational trials.

In summary, single oral doses of 5, 10, and 20 mg famotidine were significantly more effective than placebo in preventing food- beverage-induced heartburn and related upper gastrointestinal symptoms when given 1 hour before a provocative meal challenge. The tolerability of three dosages of famotidine was comparable to that of placebo.

What is claimed is:

1. A method for preventing heartburn episodes in a patient susceptible to suffering heartburn episodes following ingestion of heartburn-inducing food or beverage, comprising administering to the patient, 30 minutes prior to consumption by the patient of the food or beverage, a composition comprising an amount of famotidine of 10 mg.

\* \* \* \* \*